United States Patent
Adams et al.

(10) Patent No.: US 12,383,436 B2
(45) Date of Patent: Aug. 12, 2025

(54) TRANSFER HEAD, METHOD AND APPARATUS FOR TRANSFERRING A PAD FROM A PICK-UP LOCATION TO A DROP-OFF LOCATION

(71) Applicants: ONTEX BV, Buggenhout (BE);
ONTEX GROUP NV, Erembodegem (BE)

(72) Inventors: Christian Adams, Kreuznick (DE);
Thomas Heege, Düngenheim (DE)

(73) Assignees: ONTEX BV, Buggenhout (BE);
ONTEX GROUP NV, Erembodegem (BE)

( * ) Notice: Subject to any disclaimer, the term of this patent is extended or adjusted under 35 U.S.C. 154(b) by 0 days.

(21) Appl. No.: 18/027,448

(22) PCT Filed: Sep. 23, 2021

(86) PCT No.: PCT/EP2021/076256
§ 371 (c)(1),
(2) Date: Mar. 21, 2023

(87) PCT Pub. No.: WO2022/063927
PCT Pub. Date: Mar. 31, 2022

(65) Prior Publication Data
US 2023/0329921 A1 Oct. 19, 2023

(30) Foreign Application Priority Data

Sep. 24, 2020 (EP) .................................. 20198198
Jan. 22, 2021 (EP) .................................. 21152906

(51) Int. Cl.
*A61F 13/15* (2006.01)
*B65G 47/84* (2006.01)
*B65G 47/91* (2006.01)

(52) U.S. Cl.
CPC ...... *A61F 13/15764* (2013.01); *B65G 47/848* (2013.01); *B65G 47/915* (2013.01)

(58) Field of Classification Search
CPC .. B65G 47/915; B65G 47/252; B65G 47/848; B65G 47/32; B65G 47/244;
(Continued)

(56) References Cited

U.S. PATENT DOCUMENTS 4,767,487 A * 8/1988 Tomsovic, Jr. ... A61F 13/15764
156/256
7,770,712 B2 * 8/2010 McCabe ............... B65G 47/848
198/698

(Continued)

FOREIGN PATENT DOCUMENTS

CN 105025856 A * 11/2015 ....... A61F 13/15756
CN 106006002 A * 10/2016 ............. B65G 47/84
(Continued)

OTHER PUBLICATIONS

International Search Report and Written Opinion for PCT/EP2021/076256, mailed Jan. 25, 2022.

*Primary Examiner* — Gene O Crawford
*Assistant Examiner* — Muhammad Awais
(74) *Attorney, Agent, or Firm* — VIVICAR Law, PLLC (57) ABSTRACT

The current invention concerns a transfer head (24) configured for the transfer of a pad (6) from a pick-up location (26) to a drop-off location (62). According to the invention, the transfer head (24) comprises a support module (28) comprising a vacuum manifold, and a core module (30) comprising an elastic mean (32). The current invention also concerns a method of transferring pad (6) from a pick-up location (26) to a drop-off location (62). The current invention also concerns an apparatus for manufacturing an absorbent article using said method of transferring pad (6) from a pick-up location (26) to a drop-off location (62). The (Continued)

invention also concerns a method of manufacturing an absorbent articles using said method of transferring pad (6).

17 Claims, 3 Drawing Sheets

(58) Field of Classification Search
 CPC ............ B65G 21/2027; B65G 21/2036; B65G 29/00; B65G 29/02; A61F 13/15764; B65H 2406/33; B65H 29/241
 USPC .................. 198/471.1, 377.01, 474.1, 803.5
 See application file for complete search history.

(56) References Cited

U.S. PATENT DOCUMENTS

| | | | | |
|---|---|---|---|---|
| 8,813,351 | B2* | 8/2014 | Schoultz | B65H 39/14 29/782 |
| 8,820,513 | B2* | 9/2014 | Papsdorf | B65G 47/848 198/470.1 |
| 9,248,053 | B2* | 2/2016 | Ogasawara | A61F 13/496 |
| 9,339,418 | B2* | 5/2016 | Hamada | A61F 13/15764 |
| 9,717,634 | B2* | 8/2017 | Tameishi | A61F 13/15764 |
| 10,039,674 | B2* | 8/2018 | Wada | A61F 13/15764 |
| 10,143,597 | B2* | 12/2018 | Findley | A61F 13/15593 |
| 10,494,197 | B2* | 12/2019 | Schneider | B65H 29/241 |
| 2002/0112939 | A1* | 8/2002 | Sumi | A61F 13/15764 198/377.08 |
| 2002/0125105 | A1* | 9/2002 | Nakakado | B65G 47/848 198/471.1 |
| 2012/0186944 | A1* | 7/2012 | McCabe | A61F 13/15764 198/470.1 |
| 2013/0091998 | A1* | 4/2013 | Yamamoto | B65H 35/0006 83/152 |
| 2013/0270066 | A1* | 10/2013 | Papsdorf | B65H 39/14 198/377.01 |
| 2013/0270067 | A1* | 10/2013 | Papsdorf | B65G 47/848 198/377.01 |
| 2013/0296148 | A1* | 11/2013 | Schneider | B65G 17/323 493/3 |
| 2014/0110052 | A1* | 4/2014 | Findley | B65G 39/07 156/302 |
| 2016/0106597 | A1* | 4/2016 | Long | A61F 13/15764 198/802 |
| 2016/0376109 | A1* | 12/2016 | Schneider | B65G 47/244 198/377.02 |
| 2019/0328591 | A1* | 10/2019 | Heinz | B65B 35/24 |
| 2020/0383840 | A1* | 12/2020 | Arima | A61F 13/15764 |
| 2021/0139252 | A1* | 5/2021 | Viola | B65G 47/244 |
| 2021/0253369 | A1* | 8/2021 | Spurzem | B65G 47/915 |

FOREIGN PATENT DOCUMENTS

| | | |
|---|---|---|
| EP | 1162162 A1 † | 12/2001 |
| EP | 1228987 B1 † | 9/2005 |
| EP | 1162162 B1 | 11/2006 |

\* cited by examiner
† cited by third party

TRANSFER HEAD, METHOD AND APPARATUS FOR TRANSFERRING A PAD FROM A PICK-UP LOCATION TO A DROP-OFF LOCATION

CROSS-REFERENCE TO RELATED APPLICATIONS

This application is the national stage application of corresponding international application number PCT/EP2021/076256, filed Sep. 23, 2021, which claims priority to and the benefit of European application nos. 20198198.2 filed Sep. 24, 2020 and 21152906.0 filed Jan. 22, 2021, which are hereby incorporated by reference in their entireties.

TECHNICAL FIELD

The invention pertains to the technical field of manufacturing absorbent article. More particularly, the invention relates to a method and apparatus for transferring pads and more particularly to transferring pads using web accumulation devices. In particular, the invention relates to a transfer head used for the transferring of said pad.

BACKGROUND

Absorbent articles, such as taped diapers or pant diapers, for example, may be manufactured by a process where discrete articles, that will be referenced as pads from here on out, such as a chassis of a taped diaper or a pant diaper comprising a topsheet, a backsheet, and an absorbent core, for example, are applied to one or more moving webs of components, such as webs of front and rear belt portions, or a single web of front belt portions or rear belt portions, for example. To achieve this, a transfer wheel may be provided that comprises at least one transfer head and a frame defining a rotation axis. The transfer heads may circumnavigate about the rotation axis in an orbit. Each of the transfer heads may comprise a transfer surface that is configured to engage one or more of the pads. The transfer heads may pick up the pad at a pick-up location and place the pad at a drop-off location within the orbit. In certain instances, the transfer device may rotate the discrete articles about 90 degrees, or other suitable angles, between the pick-up location and the drop-off location about a second rotation axis that is perpendicular, or substantially perpendicular, to the rotation axis. Some transfer wheel that rotate and transfer discrete articles are known in the art as "turn and repitch" units because the units turn the discrete articles and repitch them (i.e., change the spacing or "pitch" between them) between the pick-up location and the drop-off location.

One problem in manufacturing such pads, jamming and damages on the final goods mainly often occurs with these turn and repitch units because the transfer head is often made in a rigid material to withstand the stress. Another issue is the clearance, or backlash, between the components at the pick-up location and at the drop-off location namely between the transfer heads and the feeding rollers.

The invention thereto aims to provide a method and apparatus which ensures that the transferring process is as efficient as possible notably by lowering the clearance between the different elements in the process line while maintaining sufficient robustness.

SUMMARY OF THE INVENTION

The present invention provides a transfer head configured for the transfer of a pad from a pick-up location to a drop-off location. According to the invention, the transfer head comprises a support module comprising a vacuum mean, and a core module comprising an elastic mean.

By "elastic mean" it is implied an element that has the ability, or physical property, to resist a distorting influence and return to its original size and shape when the influence or force is removed.

The term "module" refers elements or parts of the transfer head, it can also correspond to layers in the transfer head.

By "vacuum mean" it is implied an element that can guarantee a vacuum, i.e. generate a negative fluid pressure and/or a positive fluid pressure, or more specifically an element that can ensure the passage of airflow in one direction or the opposite to generate a difference of pressure, within the transfer head.

Such vacuum mean can correspond to at least one hole that can ensure that the support module, and the transfer head, is in fluid communication with a pump. The vacuum mean can also correspond to a vacuum manifold or a pump. The vacuum mean enables the transfer head to generate a negative fluid pressure and/or a positive fluid pressure.

The transfer head according to the present invention allows the transfer of the pad from a pick-up location to a drop-off location thanks to the support module that can maintain the pad onto the transfer head with the vacuum induced by the vacuum manifold and the elastic mean present in the core module enables the transfer head to adapt to the shape of the other elements in the process line, such as the feeding rolls, in order to compensate the clearance and leave no space between the transfer head and any element that can come into contact with the transfer element.

The space between the transfer element and the other elements in the process is reduced, thus there is less distance and the transfer of the pad from the roller feed to the transfer head is reduced. This improves significantly the stability of the transfer from one element to the other, there are less risk to damage the transfer head if it has a module or element that can absorb shocks.

According to an embodiment, the elastic mean comprises an elastic material. Preferably the elastic mean consists essentially of an elastic material and more preferably the elastic mean consists of an elastic material.

Preferably, the core module comprises an elastic material for example elastomers such as rubbers (synthetic and natural), thermoplastic elastomers, polysulfide rubbers. Preferably, the core module consists essentially of an elastic material for example elastomers such as rubbers (synthetic and natural), thermoplastic elastomers, polysulfide rubbers. Preferably, the core module consists of an elastic material for example elastomers such as rubbers (synthetic and natural), thermoplastic elastomers, polysulfide rubbers.

According to an another embodiment, the core module comprises a polyurethane foam and/or polyethylene foam and/or rubber foam and/or polyamide foam. Preferably, the core module consists essentially of a polyurethane foam and/or polyethylene foam and/or rubber foam and/or polyamide foam and more preferably, the core module consists of a polyurethane foam and/or polyethylene foam and/or rubber foam and/or polyamide foam According to an another embodiment of the invention, the elastic means is a spring.

According to another aspect of the invention, the transfer element further comprises an additional coating layer comprising an antiadhesive material.

Preferably, the transfer head further comprises a coating layer, said coating layer comprising an antiadhesive material, the core module being arranged between the support module and the coating layer.

Preferably, the transfer element is arranged in a way that the core module is located between the support module and the coating layer.

Preferably, the antiadhesive coating contains polytetrafluoroethylene (Teflon) and/or polysiloxane (silicone) and/or polyurethane and/or ceramics.

Preferably, the transfer head is elongated in a longitudinal direction defining a first and second longitudinal ends, the transfer head having a first rounded edge at the first longitudinal end and/or a second rounded edge at the second longitudinal end.

Preferably, the core module comprises vacuum holes.

Preferably, the coating layer comprises vacuum holes.

Preferably, the distribution of vacuum holes is higher at the first rounded edge than at the second rounded edge. In other words, there are more vacuum holes at the first rounded edge than at the second rounded edge Of course, the transfer head according to the invention is not limited to each embodiment separately and each feature mentioned above and afterwards can be taken individually or in combination.

The invention also concerns a method of transferring a pad from a pick-up location to a drop-off location, the method comprising:
  providing a transfer device having a frame with a center defining a rotation axis, wherein the transfer device comprises at least one transfer head as described above;
  circumnavigating the plurality of transfer heads about the rotation axis in an orbit, wherein the orbit passes through the pick-up location and the drop-off location;
  providing a feeding line to convey one or two web lines proximate to the drop-off location,
  using one of the plurality of transfer heads to pick up a pad at the pick-up location;
  carrying the pad on the one of the plurality of transfer heads between the pick-up location and the drop-off location; and
  placing the pad onto a portion of the web in the drop-off location.

Preferably, the transfer head provides a negative fluid pressure to the pad at the pick-up location and/or a positive fluid pressure to the pad at the drop-off location.

The invention also concerns an apparatus for manufacturing an absorbent article comprising
  a transfer device for transferring a pad from a pick-up location to a drop-off location, said transfer device having a frame with a center defining a rotation axis and at least one arm, wherein the transfer device comprises at least one transfer head as described above
  a feeding roll arranged to feed said transfer device with a continuous web of pad at the pick-up location,
  a feeding line to convey one or two web lines proximate to the drop-off location.

Preferably, the feeding roll and the transfer device are arranged in such way that at the pick-up location, the core module of the transfer head is adapted to be deformed by the pad and/or the feeding roll.

The invention also concerns a method of manufacturing an absorbent articles, the method comprising:
  forming a continuous web of pads by assembling a back sheet layer, a top sheet layer and an absorbent core between said back sheet layer and top sheet layer;
  cutting said continuous web of pads into individual pads with separation means;
  transferring said pad from a pick up location to a drop off location using the method of transferring a pad described above;
  cutting the web with a separation device to form an absorbent article.

Further embodiments are described below and in the claims.

DETAILED DESCRIPTION OF THE INVENTION

The current invention concerns a transfer head configured for the transfer of a pad from a pick-up location to a drop-off location. The current invention also concerns a method of transferring a pad from a pick-up location to a drop-off location. The current invention also concerns an apparatus for manufacturing an absorbent article using said method of transferring a pad from a pick-up location to a drop-off location.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:
  "A", "an", and "the" as used herein refers to both singular and plural referents unless the context clearly dictates otherwise. By way of example, "a compartment" refers to one or more than one compartment.
  "About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.
  "Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

Figure 1:
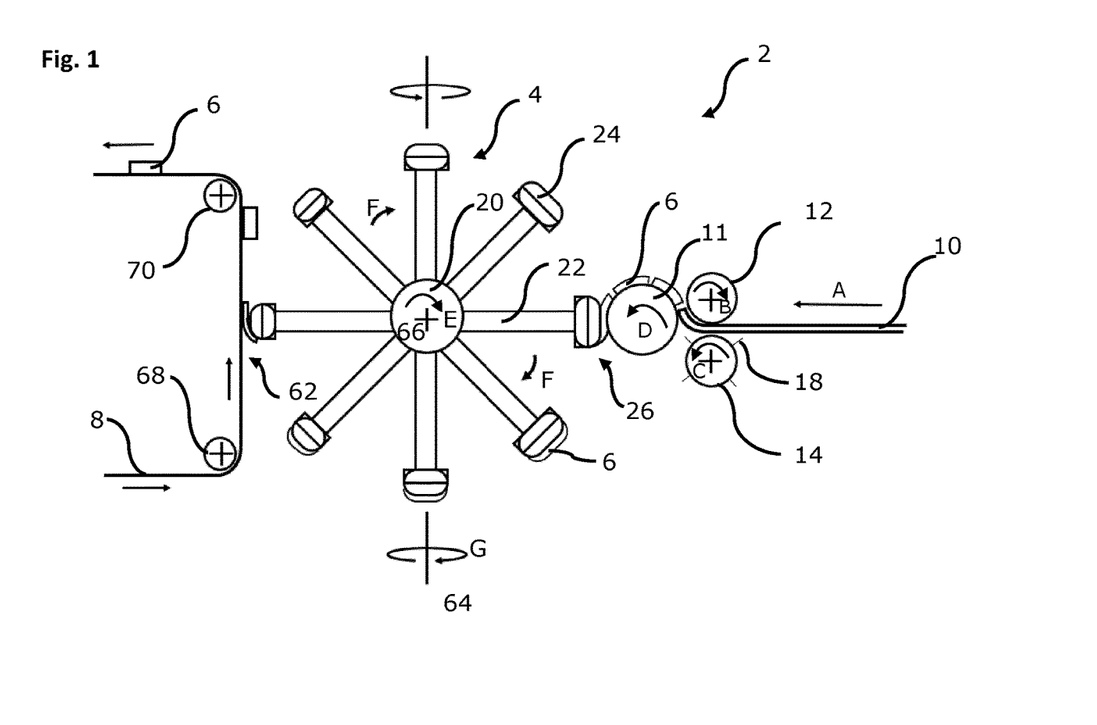
FIG. 1 illustrates schematically from a side view a module, or a part, of the process to manufacture an absorbent article in accordance with an embodiment of the present invention.

FIG. 1 illustrates schematically from a side view a module, or a part, of the process to manufacture an absorbent article, in accordance with an embodiment of the present invention. FIG. 1 shows namely the transfer assembly 2 of a pad 6. Here, the transfer assembly 2 comprises a transfer device 4 configured to transfer one or more pads 6 to one or more webs 8. The pad 6 being transferred may be a chassis of an absorbent article, such as a diaper, a pant, or adult incontinence product. The chassis of an absorbent article may comprise a topsheet, a backsheet, and an absorbent core positioned at least partially intermediate the topsheet and the backsheet. The chassis may also comprise one more acquisition material and/or distribution material at least partially intermediate the topsheet and the absorbent core. The chassis may also comprise one or more pairs of leg cuffs. The webs 8 being conveyed may be front and rear belts that attach to ends of the chassis. In other instances, a single belt (e.g., a rear belt) may be attached to only one end of the chassis.

Starting on the right end side of the example transfer assembly 2 of FIG. 1, a continuous web of pad 10 is conveyed in the direction (A) of the transfer device 4, here from right to left. To do this, the transfer assembly 2 comprises conveying means 11,12,14 corresponding here to a first roll 11 which acts as a feeding roll 11, a second roll 12 which acts as a cutting roll 12 and a third roll 14 which acts as an anvil 14 for the cutting roll 12. Of course, the transfer assembly 2 may comprise further conveying means. The transfer assembly may also comprise less conveying means, for example the feeding roll 11 can act as a feeding roll and as an anvil for the cutting roll 12 altogether. The web of pads may be separated into individual pads 6 by the separation means 12,14. The anvil roll 14 is configured to transfer each pad 6 to the feeding roll 11 and may also act as an anvil for the cutting roll 12. The cutting roll 12 comprises one or more knives 18 depending on the desired pad length. The anvil roll 14 and the cutting roll 12 rotate in opposite directions, namely the anvil roll 14 rotates in a clockwise direction (represented by arrow B) and the cutting roll 12 rotates in the counter clockwise direction (illustrated by arrow C). As the cutting roll 12 rotates, each of the knives 18 comes into contact with the continuous web of pads 10 and presses against the anvil roll 14 to separate each single pad 6 and allow the single pad 6 to move onto the feeding roll 11. The feeding roll 11 rotates in an opposite direction than the anvil roll 14, i.e. in a counter clockwise direction (illustrated by arrow D). The web of pads 10 passes between the cutting roll 12 and the anvil roll 14 where it is separated into individual pads 6. Each pad 6 then passes between the anvil roll 14 and the feeding roll 11. This way, the different rolls 11,12,14 can induce the movement of the pads 6 from the web of pads 10 to the transfer device 4, of course the invention is not limited to this specific embodiment and the rolls can be arranged differently. In some instances, individual pads 6 may be conveyed toward the feeding roll 11 without a separation device.

The feeding roll 11 may have vacuum to hold the individual pads 6 unto its surface until the pad is transferred to the transfer device 4. The transfer device 4 comprises a frame 20 with a center and a plurality of arms 22. A transfer head 24 is located at the end of each arm 22. Each individual pad 6 is applied onto a transfer head 24 that guides the pad 6 from a pick-up location to a drop-off location. During transfer between the feeding roll 11 and the transfer head 24, the feeding roll 11 may apply a positive fluid pressure to the pad, portions thereof, to blow on the pad and cause the pad 6 to transfer to a transfer head 24. During transfer between the feeding roll 11 and the transfer head 24, the transfer head 24 may apply a negative fluid pressure to the pad, portions thereof, to suck on the pad and cause said pad 6 to stay on the surface of the transfer head 24. Of course both embodiments can be combined.

Figure 2:
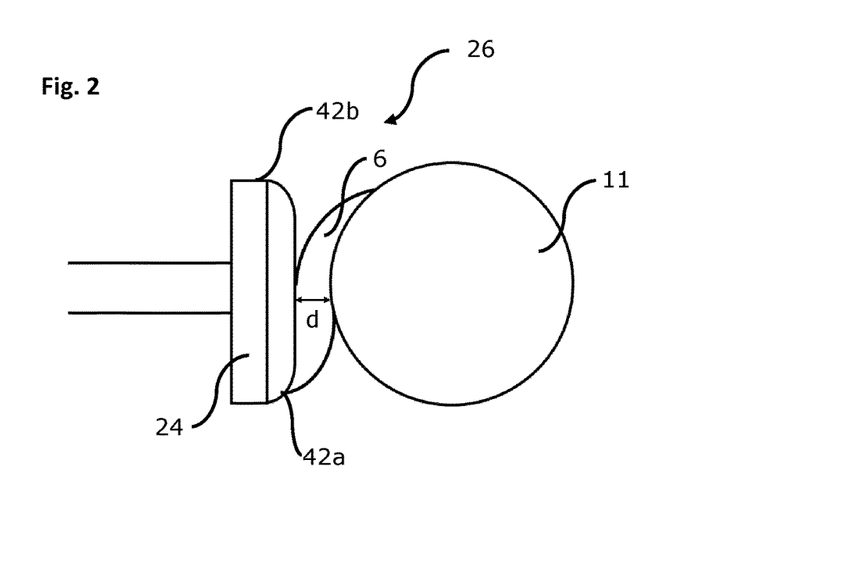
FIGS. 2 and 3 both illustrate a close-up of the module in FIG. 1, namely the pick-up location at different stage of transfer of the pad.
Figure 3:
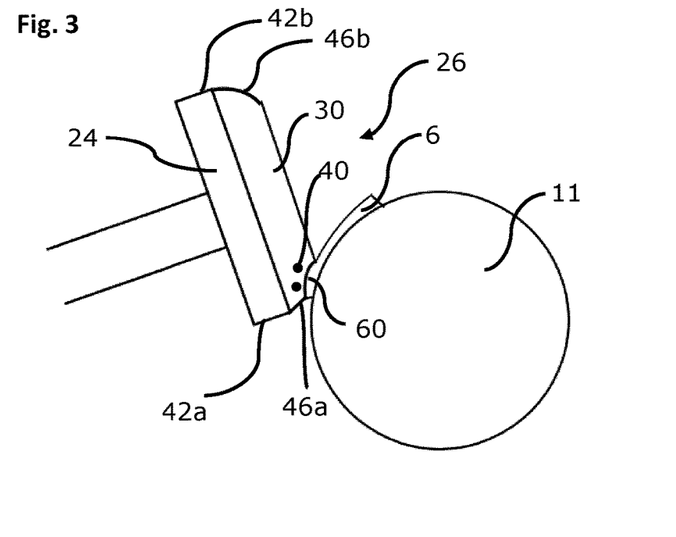

The transfer between the feeding roll 11 and the transfer head 24 is an important step regarding the efficiency of the transfer process and is located at a point that will be called the pick-up location 26 from here on out. FIG. 2 and FIG. 3 both illustrate a close-up of said pick-up location 26 at different stage of the transfer of the pad 6. FIG. 2 represents the pick-up location 26 at when the pad 6 is halfway transferred onto the transfer head 24. Whereas FIG. 3 illustrates the pick-up location 26 at a timepoint beforehand notably when the pad 6 is starting to be transferred onto the transfer head 24.

As illustrate on FIG. 2, when the pad 6 is halfway into contact with the transfer head 24, the feeding roll 11 is separated from the transfer head 24 by a distance d which represents approximately 10 mm, said distance d correspond to the clearance necessary for the transfer head 24 being able to pass and pick up the pad 6. Because of that distance d, the transfer of the pad 6 from the feeding roll 11 unto the transfer head 24 takes a few microseconds which can create an instability and possible jamming in the process. Thus in order to have an efficient transfer assembly, the distance d must be as small as possible in order to limit the time of transfer between the feeding roll 11 and the transfer head 24. The issue with a conventional transfer device 4 is that this distance d cannot be lowered. Indeed, increasing the radius of the transfer device 4, or in other words increasing the lengths of the arms 22, to bring the transfer head 24 closer to the feeding roll 11 is not possible because the transfer head, 24 when rotating around the axis of the frame 20 with a center, will hit the feeding roll 11 and get damaged.

Thus in order to improve the transfer of a pad 6 from a feeding roll 11 to the transfer head 24, the invention provides a transfer head 24 configured to transfer a pad 6 from a pick-up location 26 to a drop-off location 62, said transfer head 24 comprises a support module comprising a vacuum mean, and a core module comprising an elastic mean.

By "elastic mean" it is implied an element that has the ability, or physical property, to resist a distorting influence and return to its original size and shape when the influence or force is removed.

By "vacuum mean" it is implied an element that can guarantee a vacuum, i.e. generate a negative fluid pressure and/or a positive fluid pressure, or more specifically an element that can ensure the passage of airflow in one direction or the opposite to generate a difference of pressure, within the transfer head. The vacuum mean can ensure a vacuum with a negative fluid pressure going from −2 kPa up to −20 kPa. The vacuum mean can ensure a vacuum with a positive fluid pressure going from 2 kPa up to 20 kPa.

Such vacuum mean can correspond to at least one hole that can ensure that the support module, and the transfer head, is in fluid communication with a manifold and/or pump. The vacuum mean can also correspond to a vacuum manifold or a pump. The vacuum mean enables the transfer head to generate a negative fluid pressure and/or a positive fluid pressure within its structure.

Figure 4:
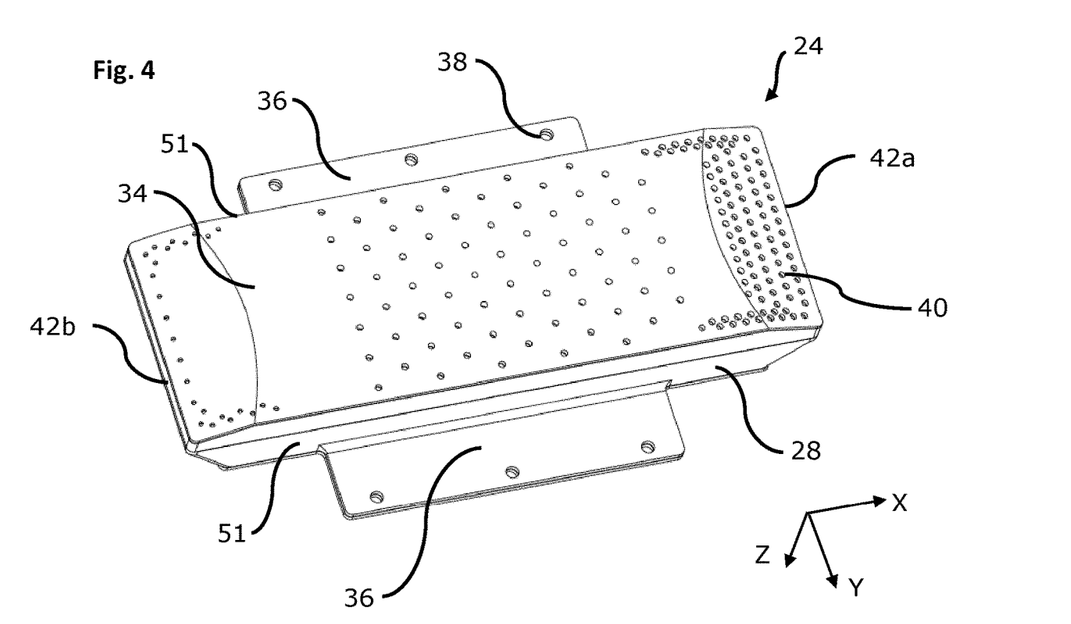
FIGS. 4 and 5 both illustrate the transfer head according to the invention.

The transfer head 24 as illustrated in FIG. 4 comprises a support module 28 which can correspond to a casing, or container, that can be made of a robust material such as plastic or metal. The support module 28 comprises a vacuum mean (not illustrated) to ensure a negative fluid pressure and enable the pad 6 to get sucked onto the transfer head 24. For example, the support module 28 can present holes so that the support module 28 is in fluid communication with a vacuum manifold or pump that can suck or blow air within the support module 28 and the transfer head 24. The transfer head 24 according to the invention also comprises a core module 30 comprising an elastic mean 32. The elastic mean 32 enables the core module to be deformed under a distorting influence and to return to its original shape once the influence is removed. The elastic mean can be mechanical and correspond to one or more springs, preferably compression springs such as leaf spring or coil spring. The elastic mean can also be chemical and correspond to the core module 30 comprising an elastic material such as elastomers rubbers (synthetic and natural), thermoplastic elastomers, polysulfide rubbers. According to another embodiment of the invention, the core module 30 comprises of a Polyurethane (PU) foam and/or Polyethylene (PE) foam and/or rubber foam and/or Polyamide (PA) foam. PU foams have the advantage of being lighter than the other embodiment (spring or rubbers) and have an excellent ability to revert to its original shape.

According to another aspect of the invention, the transfer head 24 further comprises an additional coating layer 34 comprising an antiadhesive coating. The antiadhesive coating improves the deposit of the pad 6 onto the webs 8 at the drop-off location by ensuring that the pad 6 does not stay stuck onto the transfer head 24. The antiadhesive coating may correspond to a layer of Polytetrafluoroethylene (Teflon) and/or polysiloxane (silicone) and/or polyurethane and/or ceramics.

According to another aspect of the invention, each transfer head 24 is attached to an arm 22 of the frame of the transfer device 4. The support module 28 can be directly fixed to the arm 22 or the transfer head 24 can further comprise a fixation plate 36 made out of robust material such as plastic or metal with fixation means 38, for example a plurality of holes as illustrated in FIG. 4, threaded or not, to enable a rod, threaded or not, to screw the fixation plate onto the arm 22 of the frame of the transfer device 4. Of course the fixation means 38 are not limited to this embodiment and can correspond to other fixation elements such as clips, snap-fits, glue for example. The support module 28 and the fixation plate 36 can be in one single piece, or unitary piece, i.e. form a continuity of matter. It is understood from this description, that the support module 28 and the fixation plate 36 are made out of a material that is more robust than the core module 30 and the coating layer 34.

According to another aspect of the invention, the transfer head 24 is arranged in a way that the core module 30 is located between the support module 28 and the coating layer 34. Furthermore, should the transfer head 24 comprise a fixation plate 36 that is distinct from the support module 28, then the transfer head 24 is arranged in a way that the fixation plate at the lowest point of the transfer head 24. The support module 28 is then located on the fixation plate 36, between the fixation plate 36 and the core module 30. The core module 30 is placed on the support module 28, between the support module 28 and the coating layer 34. The coating layer 34 is recovering the core module 30.

The fixation plate 36 and the support module 28 can be made as an unique single piece or as two separate parts. The fixation plate 36 and the support module 28 can be made in the same material or of two different materials. For example, the transfer head 24 can comprise a fixation plate 36 made out of metal and a support module 28 made out of plastic.

As illustrated on FIG. 4, the transfer head comprises vacuum holes 40, or fluid ports. These vacuum holes are present within the coating layer 34 and the core module 30 and enable the vacuum manifold to ensure the negative fluid pressure more efficiently and ensure that the pad stays more securely on the surface of the coating layer 34.

As illustrated on FIG. 4, the transfer head 24 extends in longitudinal (X), transverse, or transversal, (Y) and vertical (Z) directions. The support module 28, core module 30 and coating layer 34 extends more in the longitudinal direction in than the transversal and vertical directions. In other words, the transfer head 24 has an elongated shape in the longitudinal direction. The transfer head 24 has two ends in the longitudinal direction 42a,42b. The first longitudinal end 42a correspond to the end of the transfer head 24 that first comes into contact with the pad 6 as illustrated in FIG. 2 at the pick-up location 26. The second longitudinal end 42b correspond to the end of the transfer head that comes last into contact with the pad 6. As illustrated in FIG. 4, the distribution, or density, of vacuum holes is different between the first longitudinal end 42a and the second longitudinal end 42b. In other words, the first and second longitudinal ends 42a,42b do not have the same numbers of vacuum holes. Specifically, the first longitudinal end 42a has a larger distribution of vacuum holes than the second longitudinal end 42b or in other words there are more vacuum holes 40 at the first longitudinal end 42a than at the second longitudinal end 42b. Indeed, when coming into contact with the pad, the first longitudinal end 42a being the first to come into contact, it will improve the adhesion of the pad onto the transfer head 24, given that having more vacuum holes will increase the negative fluid pressure.

Figure 5:
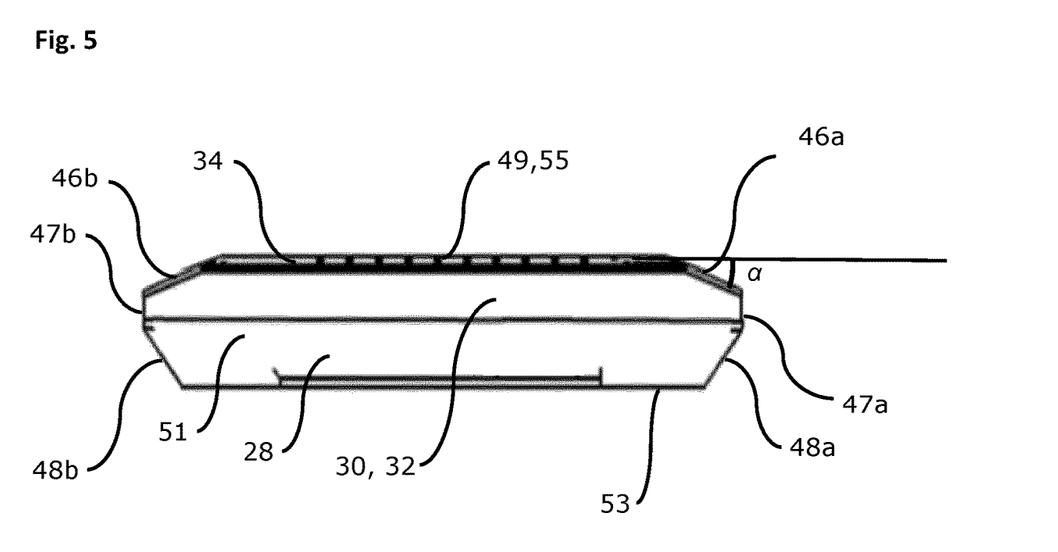

As illustrated in FIGS. 4 and 5, the transfer head 24 can have rounded edges 46a,46b,48a,48b at each longitudinal ends 42a,42b. More specifically, the core module 30 has rounded edges 46a,46b at each longitudinal ends 42a,42b. This ensures that the rotation of the transfer head 24 is less impeded by the feeding roll 11, this will be further explained afterwards. Optionally, the support module 28 can also present rounded edges 48a,48b. The first rounded edge 46a correspond to the edge of the transfer head, specifically of the core module 30 at the first longitudinal end 42a. The second rounded edge 46b correspond to the edge of the transfer head, specifically of the core module 30 at the second longitudinal end 42b. The same logics applies to the rounded edge 48a,48b of the support module 28.

As illustrated on FIG. 5, the core module 30 has a section in a shape of an irregular hexagon. The transfer head 24 and notably the support module 28 and the core module 30 have the shape of a rectangular prism that has two longitudinal surfaces, or sides, 47a,47b at the end longitudinal ends (X-direction), two transversal surfaces, or sides, 51 at the transversal ends (Y-direction) and a top surface, or top side, 49 and bottom surface, or bottom side 53 (Z-direction). The longitudinal surfaces 47a,47b are two parallel planes that each extends in the transverse (Y) and vertical (Z) directions and are apart in the longitudinal direction (X) thus defining the length of the transfer head 24. Same as the transversal surfaces 51 that are two parallel planes that each extend in the longitudinal (X) and vertical (Z) directions and are apart in the transverse direction (Y) thus defining the width of the transfer head 24. Same as the top side 49 and bottom side 53 that are two parallel planes that each extend in the longitudinal (X) and transversal (Y) directions and are apart in the vertical direction (Y) thus defining the height of the transfer head 24. As explained previously, the transfer head 24 has rounded edges. Namely the longitudinal surfaces 47a,47b are adjoined to the top (49) and/or bottom (51) surfaces by a chamfer (46a,46b,48a,48b). In order words, a chamfer 46a links a longitudinal surface 47a to the top side 49 of the transfer head 24, i.e. an inclined plane 46a, or slope, makes the transition between the top side 49 and a longitudinal surface 47a. It can also be said that the top side 49 and the longitudinal side 47a have edges that are softened by an inclined plane. The inclined plane 46a, can be at an angle α (noted afterwards in degrees) that is comprised in a range between 25 degree and 70 degree included, preferably an angle between 35 degree and 55 degree, more preferably at an angle between degree and 50 degree. This prevents damage to the edges of the transfer head 24. Of course the invention is not limited to this embodiment, in the sense that there can be one or more inclined planes to soften the edges. The rounded edge 46a can also corresponds to a convex non-tangent rounding or concave fillet or any other smooth transition replacing the single edge between the top 49 and longitudinal 47a surfaces and having an arc-shaped cross-section. Of course, there can be a rounded edge 46b between the other longitudinal surface 47b and the top surface 49 as well as a rounded edge 48a,48b between each longitudinal surface 47a,47b and the bottom surface 53. More specifically, the core module 30 has rounded edges 46a,46b between the top side 49 and the longitudinal surfaces 47a,47b, the coating layer 34, being a covering layer on the core module 30, adopts the same contour, or shape, as the core module 30. The support module 28 can also have rounded edges 48a,48b between the bottom side 53 and the longitudinal surfaces 47a,47b. The middle portion 55 of the top surface 49 located between the rounded edges 46a,46b is sensibly flat as illustrated on FIG. 5. It is also possible for example that the transition between the top side 49 and the longitudinal side 47 corresponds to a beveled edge where the longitudinal end 42a,42b corresponds to the support module 28 and the core module 30 doesn't present any flat surface at the longitudinal end 42a,42b, i.e. directly links the longitudinal surface 47a, 47b which corresponds to the support module 28 to the top surface 49.

The support module 28 can be in the form of a container, i.e. a element with side walls and a bottom wall and defining a hollow space, the core module 30 can be partially received in said hollow space and protrude from the support module 28 on the side opposite of the bottom wall. The coating layer 34 covering the part of the core module 30 destined to receive the pad 6, i.e the side that is opposite of the bottom wall contained in the hollow space. The support module 28 can also be in the form of a solid plate, with a flat surface and no hollow space, with the core module 30 laying onto the plate, the coating layer 34 being arranged on the side of the core module 30 that is opposite to the side of the core module 30 laying against the solid plate of the support module 28. Of course it is also possible to have the support module as plate with a part protruding, the core module recovering said plate and protruding part. The support module 28 is 5 to 20 mm thick (in the z direction), preferably 10 to 15 mm high, the core module 30 is 20 to 70 mm thick (in the z direction), preferably 40 to 60 mm thick and the coating layer 34 is 0.5 to 5 mm thick.

In any instance, the support module 28 comprises vacuum means. The support module 28 can have holes in the bottom wall or in the solid plate mentioned above so that the bottom part of the support module can be in fluid communication with a vacuum pump that can suck or blow air. The core module and the coating layer 34 also comprise vacuum holes 40 to enable the vacuum generated within the support module 28 to reach the surface destined to receive the pad 6. For example, a vacuum pump can be arranged within the frame 20 with a center, the arms 22 can be hollow and the air can be either sucked from or blown into the transfer head 24 through the holes in the support module 28 and core module 30 and coating layer 34 to generate a negative or positive fluid pressure. It is also possible to arrange a vacuum manifold within the support module 28 to ensure the generation of a negative or positive fluid pressure.

As illustrated on FIG. 4, the vacuum holes 40 are present on the top surface 49 and the distribution of vacuum holes 40 is more important on the first rounded edge 46a located at the first longitudinal end 42a. The distribution of vacuum holes 40 on the middle portion 55 is lower than on the first rounded edge 46a. The distribution of vacuum holes 40 on the second rounded edge 46b located at the second longitudinal end 42b is lower than on the middle portion 55. In other words, the distribution of vacuum holes 40 varies, in particular decreases, from the first longitudinal end 42a to the second longitudinal end 42b. In other words, there are more vacuum holes 40 at the first rounded edge 46a than at the second rounded edge 46b.

The principle as described above can be applied to the transversal ends 51, in the sense that transversal ends can have rounded edges between the transversal sides 51 and the top surface 49 and/or bottom surface 53. The distribution of vacuum holes 40 can also varies from one first transversal end to the second transversal end.

The combination of the shape and the distribution of vacuum holes on the transfer head enables a proper vacuum which improves the maintaining of the pad 6 onto the transfer head 24. The combination of the elastic mean and the shape of the transfer head enable the transfer head 24 to get closer to the feeding roll 11, i.e. reduce the distance d, and improve the transfer of the pad 6 at the pick-up location 26.

The transfer head 24 according to the present invention allows a better transfer of the pad 6 from a pick-up location 26 to a drop-off location 62 thanks to the support module 28 that can maintain the pad 6 onto the transfer head 24 with the vacuum induced by the vacuum mean and the elastic mean 32 present in the core module 30 enables the transfer head 24 to adapt to the shape of the feeding roll 11, in order to compensate the clearance d and leave little to no space between the transfer head 24 and any element that can come into contact with the transfer head. In order words, it is possible to reduce the distance d between the transfer head 24 and the feeding roll 11 without a risk of damaging the transfer head 24. Indeed, the core module 30 presenting an elastic mean 32 can absorb the deformation. It is also possible that if the feeding roll 11 is set to go too fast and delivers two pads 6 instead of one, a conventional transfer head will not be able to handle this event which will cause a jamming and damaging to the transfer head. Indeed, a pad 6 being 4-5 mm thick, the clearance d needed between the feeding roll 11 and the transfer head 24 will not be respected. Whereas, with the transfer head 24 according to the invention, the elastic mean 32 will deform and absorb this extra thickness, and it will be able to deliver the pad 6 at the drop-off location.

FIG. 3 illustrates the pick-up location 26 at a timepoint when the pad 6 is starting to be transferred onto the transfer head 24. The core module 30 comprising an elastic mean, notably the core module 30 being made out of a PU foam and/or PE foam and/or PA foam and/or Rubber foam can be compressed. Therefore, it is possible to bring the transfer head 24 closer to the feeding roll 11 given that the core module 30 can withstand, or absorb, the deformation influence. The pad 6, being carried by the feeding roll 11, comes into contact with the transfer head 24, in particular with the core module 30, at the first longitudinal end 42a of the transfer head 24. The transfer head 24, being closer to the feeding roll 11, the distance between the feeding roll 11 and the support module 28 creates a nip, or a pinch, where the pad 6 and the core module 30 are pressed together, the elastic mean 32 enabling a deformation 60 of the core module 30, the additional vacuum holes 40 on the first rounded edge 46a at the first longitudinal end 42a, all of the features allow improved maintaining of the pad 6 onto the transfer head 24, and/or reduce the risk of jamming of the transfer assembly 2 in a cost efficient manner.

To sum up, the space between the transfer head 24 and the other elements in the process is reduced, thus the distance d and the transfer time of the pad 6 from the roller feed 11 to the transfer head 24 is reduced. This improves significantly the stability of the transfer from one element to the other, there are less risk to damage the transfer head 24 given that there is a layer, the core module 30, that can absorb shocks. Indeed the elastic mean 32 will be deformed by the feeding roll 11 and will revert back its original shape once the transfer head 24 has passed the feeding roll 11. The same principle applies with the second longitudinal ends 42b, where the second rounded edges 42b and the elastic means 32 improve the maintain of the pad 6 onto the transfer head 24.

The transfer device 4 is the apparatus that is configured to turn and repitch the pad 6, turn the discrete articles, or merely transfer the pad 6 between a pick-up location 26 and a drop-off location 62. The transfer device 4 may comprise a frame 20 with a center, such as a wheel, defining a rotation axis 66, rotating here in a clockwise direction (arrow E), and a plurality of arms 22, or branches, each carrying a transfer head 24. The transfer heads 24 are configured to circumnavigate about the rotation axis 66 in an orbit. The orbit passes through the pick-up location 26 and the drop-off location 26. The transfer heads 24 orbit in the same direction as the frame 20 with a center illustrated by arrows F, here in the clockwise direction. Each of the transfer heads 24 as described above comprise core module 30 and a coating layer 34 (the pad 6 receiving surface) having a plurality of fluid ports 40 defined therein. The vacuum holes 40 are configured to provide a negative fluid pressure and/or a positive fluid pressure to the pad 6 being carried on the transfer heads 24. The negative fluid pressure is used to maintain the pad 6, or portions thereof, onto the receiving surface at the pick-up location 26 and during orbiting of the transfer heads 24. The positive fluid pressure may be used to blow-off the pad 6, or portions thereof, at the drop-off location 62 onto the webs 8. The transfer heads 24 may have the same speed or substantially the same speed as the feeding roll 11 at the pick-up location 26 and/or as the web 8 at the drop-off location 62 to promote smooth transfer of the pad 6.

The turn and repitch transfer device 4 can also turn the pad 6 (arrows G) at any suitable angle, around an axis 64 that is perpendicular to the rotation axis 66 of the frame 20 with a center, between the pick-up location 26 and the drop-off location 62. For example, the transfer device 4 may turn the pad 6 about a certain degree in the range of about 40 degrees to about 140 degrees, preferably at an angle of 90 degrees specifically reciting all 0.5 degree increments within the specified range. The pads 6 are turned by the rotation of the transfer heads 24. For example, a transfer head 24 may pick up a pad 6 at the pick-up location 26, turn 90 degrees about an axis 64 that is perpendicular to the rotation axis 66 of the frame 20 with a center, drop off the pad 6 at the drop-off location 62, and the turn back to its original position (either in the same direction or an opposite direction) before orbiting back at the pick-up location 26. In addition to the turning, the pad 6 may be repitched intermediate the pick-up location 26 and the drop-off location 62. The transfer device 4 may circumnavigate the transfer heads 24 at a constant angular velocity or a variable angular velocity as the transfer heads 24 orbit the rotation axis 66.

The pad 6 is then guided at the drop-off location 62, where the pad 6 comes into contact with a continuous line or feed of web 8. The web 8 can comprise two line of webs, such as front and rear belts, while other web accumulation devices may be configured to handle only one web, such as only front belts or only rear belts. The web comprises adhesive on its surface so that when the pad 6 comes into contact with the web 8, it stays onto the web. The continuous line of web 8 can be conveyed by feeding means such as two or more rolls 68,70 as illustrated in FIG. 1. The transfer head having a plurality of fluid ports 40 as defined above, the vacuum holes 40 are configured to provide a positive fluid pressure to the pad 6 at the drop-off location 62 to blow-off the pad 6, or portions thereof, onto the webs 8. The coating layer 34 being an antiadhesive silicone layer improves this transfer and cannot get stuck onto the adhesive of the web 8.

In one embodiment, the transfer heads 24 define a plurality of vacuum holes 40 or fluid ports. A first fluid movement device may be in fluid communication with a first fluid line and a second fluid movement device may be in fluid communication with a second fluid line. Both of the fluid lines may supply fluid to a fluid receiving manifold that can be located at the center of the frame 20. Fluids may be supplied to the fluid ports in the transfer heads 24 through fluid lines that extend from the fluid manifold to the transfer heads through recesses defined in the frame 20 and arms 22. One of the fluid movement devices may supply a positive fluid pressure and the other fluid movement device may supply a negative fluid pressure, or both may cycle between supplying a positive fluid pressure and negative fluid pressure. The negative fluid pressure may be used to maintain the pad 6 on the transfer head 24 and the positive fluid pressure may be used to blow-off the pad 6 from the transfer head 24 onto the web 8 at the drop-off location.

The transfer head according to the invention thus ensure a smooth receiving and delivery of the pad 6 with no loss of vacuum.

After the drop-off location 62, the pad 6 and web 8 will be cut and separated into individual absorbent articles such as diaper or an incontinence pant.

The invention also concerns a method of manufacturing an absorbent articles, the method comprising:
  forming a continuous web of pads 10 by assembling a back sheet layer, a top sheet layer and an absorbent core between said back sheet layer and top sheet layer;
  cutting said continuous web of pads 10 into individual pads 6 with separation means 12,14;
  transferring said pad 6 from a pick up location to a drop off location using the method as described above;
  cutting the web 8 with a separation device to form a absorbent article.

The invention claimed is:

1. A transfer head (24) configured for the transfer of a pad (6) from a pick-up location (26) to a drop-off location (62), wherein the transfer head (24) comprises
  a support module (28) comprising a vacuum mean, and
  a core module (30) comprising an elastic mean (32),
    wherein the transfer head (24) is elongated in a longitudinal direction (X) defining first and second longitudinal surfaces (47a,47b) at first and second longitudinal ends (42a,42b) and has a top surface (49) and a bottom surface (53) in a vertical direction (Z) and two transverse sides (51) in a transverse direction (Y), the core module (30) having a first rounded edge (46a) at the first longitudinal end (42a) and a second rounded edge (46b) at the second longitudinal end (42b), the support module (28) having a first rounded edge (48a) at the first longitudinal end (42a) and a second rounded edge (48b) at the second longitudinal end (42b), such that the first and second longitudinal surfaces (47a,47b) are adjoined to the top surface (49) and the bottom surface (53) by a chamfer (46a,46b,48a,48b).

2. Transfer head (24) according to claim 1, wherein the elastic mean (32) comprises an elastic material.

3. Transfer head (24) according to claim 2, wherein the core module (30) comprises a polyurethane foam and/or polyethylene foam and/or rubber foam and/or polyamide foam.

4. Transfer head (24) according to claim 1 wherein, the transfer head (24) further comprises a coating layer (34), said coating layer comprising an antiadhesive material, the core module (30) being arranged between the support module (28) and the coating layer (34).

5. Transfer head (24) according to claim 4, wherein the antiadhesive material contains polytetrafluoroethylene and/or silicone and/or polyurethane.

6. Transfer head (24) according to claim 4, wherein the coating layer (34) comprises vacuum holes (40).

7. Transfer head (24) according to claim 1, wherein, the core module (30) comprises vacuum holes (40) and the distribution of vacuum holes is higher at the first rounded edge (46a) than at the second rounded edge (46b).

8. A method of transferring a pad (6) from a pick-up location (26) to a drop-off location (62), the method comprising:

providing a transfer device (4) having a frame (20) with a center defining a rotation axis (66), wherein the transfer device (4) comprises at least one transfer head (24) according to claim 1;

circumnavigating the plurality of transfer heads (24) about the rotation axis (66) in an orbit, wherein the orbit passes through the pick-up location (26) and the drop-off location (62);

providing a feeding line (68,70) to convey one or two web lines (8) proximate to the drop-off location (62), using one of the plurality of transfer heads (24) to pick up a pad (6) at the pick-up location (26);

carrying the pad (6) on the one of the plurality of transfer heads (24) between the pick-up location (26) and the drop-off location (62); and placing the pad (6) onto a portion of the web (8) in the drop-off location (62).

9. Method according to claim 8, wherein the transfer head (24) provides a negative fluid pressure to the pad (6) at the pick-up location (26) and/or a positive fluid pressure to the pad (6) at the drop-off location (62).

10. An apparatus for manufacturing an absorbent article comprising a transfer device (4) for transferring a pad (6) from a pick-up location (26) to a drop-off location (62), said transfer device (4) having a frame (20) with a center defining a rotation axis (66) and at least one arm (22), wherein the transfer device (4) comprises at least one transfer head (24) according to claim 1;

a feeding roll (11) arranged to feed said transfer device (4) with a continuous web of pad (6) at the pick-up location (26), a feeding line (68,70) to convey one or two web lines (8) proximate to the drop-off location (62).

11. Apparatus according to claim 10, wherein the feeding roll (11) and the transfer device (4) are arranged in such way that at the pick-up location (26) the core module (30) of transfer head (24) is deformed by the pad (6) and/or the feeding roll (11).

12. A method of manufacturing an absorbent article, the method comprising:

forming a continuous web of pads (10) by assembling a back sheet layer, a top sheet layer and an absorbent core between said back sheet layer and top sheet layer;

cutting said continuous web of pads (10) into individual pads (6) with separation means (12,14);

transferring said pad (6) from a pick up location (26) to a drop off location (62) using the method according to claim 10; cutting the web (8) with a separation device to form an absorbent article.

13. Transfer head (24) according to claim 6, wherein, the distribution of vacuum holes is higher at the first rounded edge (46a) than at the second rounded edge (46b).

14. Transfer head (24) according to claim 1, wherein the first rounded edge (46a) is at an angle from 25 to 70 degrees between the top surface (49) and the first longitudinal surface (47a).

15. Transfer head (24) according to claim 1, wherein the first rounded edge (46a) is at an angle from 35 to 55 degrees between the top surface (49) and the first longitudinal surface (47a).

16. Transfer head (24) according to claim 1, wherein the first rounded edge (46a) is at an angle from 40 to 50 degrees between the top surface (49) and the first longitudinal surface (47a).

17. Transfer head (24) according to claim 7, wherein the distribution of vacuum holes (40) at a middle portion (55) located between the rounded edges (46a,46b) is lower than at the first rounded edge (46a), and wherein the distribution of vacuum holes at the second rounded edge (46b) is lower than at the middle portion (55).

* * * * *